US008591402B2

(12) United States Patent
Yamakita (10) Patent No.: US 8,591,402 B2
(45) Date of Patent: Nov. 26, 2013

(54) ENDOSCOPE HOOD

(75) Inventor: Hiroshi Yamakita, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 107 days.

(21) Appl. No.: 13/075,638

(22) Filed: Mar. 30, 2011

(65) Prior Publication Data
US 2011/0245679 A1 Oct. 6, 2011

(30) Foreign Application Priority Data

Mar. 31, 2010 (JP) ................................. 2010-082253

(51) Int. Cl.
*A61B 1/00* (2006.01)
(52) U.S. Cl.
USPC ............ 600/127; 600/121; 600/129; 600/156
(58) Field of Classification Search
USPC .................. 600/104, 106, 107, 114–116, 127, 600/121–125, 128–130, 156–159, 175
See application file for complete search history.

(56) References Cited

U.S. PATENT DOCUMENTS

| 5,938,586 | A  | * | 8/1999  | Wilk et al. ..................... 600/123 |
| 6,120,437 | A  | * | 9/2000  | Yoon et al. ..................... 600/204 |
| 2004/0210278 | A1 | * | 10/2004 | Boll et al. ........................ 607/89 |
| 2004/0260147 | A1 | * | 12/2004 | Schulze ......................... 600/101 |
| 2007/0244353 | A1 | * | 10/2007 | Larsen ........................... 600/105 |
| 2008/0300460 | A1 | * | 12/2008 | Sugita ........................... 600/127 |
| 2009/0156898 | A1 |   | 6/2009  | Ichimura |

FOREIGN PATENT DOCUMENTS

| JP | 2001-275933 A | 10/2001 |
| JP | 2001-275942 A | 10/2001 |
| JP | 2003-144378 A | 5/2003 |
| JP | 2004-376 A | 1/2004 |
| JP | 2005-211433 A | 8/2005 |
| JP | 2008-54843 A | 3/2008 |

* cited by examiner

*Primary Examiner* — Matthew J Kasztejna
*Assistant Examiner* — Ryan Henderson
(74) *Attorney, Agent, or Firm* — Birch, Stewart, Kolasch & Birch, LLP (57) ABSTRACT

An endoscope hood includes: an opening portion which is placed on a far side with respect to a leading end surface of an insertion part of an endoscope, wherein an opening is formed on the opening portion in a direction substantially orthogonal to an axial direction of the insertion part; and a flexible hood part configured to cover a portion other than the opening, on the far side with respect to the leading end surface of the insertion part, wherein gas inside of the hood part is sucked from a gas suction port of the insertion part, the opening is adsorbed onto a region to be measured, and the hood part is deformed so as to be closely adhered to the region to be measured within a range of the opening and a probe, to thereby fix the probe to the region to be measured in a state where the probe is set therealong.

12 Claims, 6 Drawing Sheets

ENDOSCOPE HOOD

BACKGROUND OF THE INVENTION

1. Field of the Invention

The presently disclosed subject matter relates to an endoscope hood, and more particularly, to an endoscope hood for fixing a probe of an optical tomographic imaging apparatus, an ultrasonic diagnostic apparatus, and the like to a region to be measured at a leading end of an insertion part of an endoscope.

2. Description of the Related Art

Up to now, diagnostic imaging has been widely carried out. In the diagnostic imaging, an insertion part of an endoscope is placed to be inserted into the body cavities of a blood vessel, a bile duct, a pancreatic duct, a stomach, an esophagus, a large intestine, and the like, and a probe placed at a leading end of the insertion part is used to perform radial scanning, whereby a tomographic image of a living body is created. As an example, in an optical coherent tomography (OCT) apparatus, an elongated optical probe with a built-in optical fiber having a leading end to which an optical lens and an optical mirror are attached is used, a signal beam is emitted in a direction substantially orthogonal to an axial direction (longitudinal direction) of the optical probe, and a return beam thereof is acquired, whereby a tomographic image of a region to be measured in the direction substantially orthogonal to the optical probe is created. Further, in the OCT apparatus, the optical mirror at the leading end of the optical fiber is rotated about the axis of the probe to perform radial scanning, whereby a tomographic image of the region to be measured in a circumferential direction of the axis of the probe is created. In addition, similarly for other measurement apparatuses such as an ultrasonic diagnostic apparatus, there has been known an apparatus in which a probe placed at a leading end of an insertion part of an endoscope is used to acquire data of a region to be measured in a direction orthogonal to an axial direction, whereby a tomographic image and the like are created. The presently disclosed subject matter is not limitatively applied to the OCT apparatus, and thus can be applied to a probe of an arbitrary apparatus. In this specification, description is given mainly of the case where the presently disclosed subject matter is applied to the optical probe for OCT.

It is desirable that the probe as described above be fixed to a region to be measured at the time of data acquisition, in order to prevent disturbance of a created image and deterioration in positional accuracy from occurring. However, in the case of observation of a living body, there are disturbances such as a body motion of the living body and hand vibrations of an operator, and hence it is difficult to fix the probe to the region to be measured in a stable state by relying only on a technique of the operator. In particular, in the case of measurement inside of the living body, body motions due to pulsation and the like cannot be stopped. Therefore, it is an important issue how to cause the probe to follow the movement of the region to be measured.

Up to now, the following methods have been generally known as the method of fixing the probe to the region to be measured. That is, Japanese Patent Application Laid-Open Nos. 2001-275942 and 2005-211433 each disclose a method in which a balloon is provided near a leading end of an insertion part of an endoscope, and the balloon is inflated so as to engage with a tube wall, to thereby fix the probe. Further, Japanese Patent Application Laid-Open Nos. 2008-054843 and 2001-275933 each disclose a method in which a hood having an opened front side is provided at a leading end of an insertion part, and is pressed against the region to be measured, to thereby fix the probe.

In addition, Japanese Patent Application Laid-Open Nos. 2004-000376 and 2003-144378 each disclose a method in which a hood provided at a leading end of an insertion part is abutted against the region to be measured, the pressure inside of the hood is reduced (air is sucked therefrom), and the hood is adsorbed onto the region to be measured, to thereby fix the probe.

SUMMARY OF THE INVENTION

Incidentally, in the case of using the probe capable of radial scanning as described above, that is, the probe which acquires data of the region to be measured in the direction substantially orthogonal to the axial direction of the probe, in order to enable the probe to follow the movement of the region to be measured caused by a body motion or the like, to thereby reduce blurring of the data (blurring of a created tomographic image), it is desirable to acquire the data in the state where the probe is fixed to the region to be measured while being set along the region to be measured in the axial direction. In particular, in the case where the leading end of the insertion part of the endoscope and the probe are fixed in such a state, if only the probe can be moved or an optical system inside of a probe external cylinder can be moved in the axial direction with the leading end of the insertion part being kept fixed, it is possible to perform linear scanning with little blurring of the data and a high positional accuracy of the data acquisition position within a range of the region to be measured along which the probe is set.

Up to now, the method of using the balloon has been proposed as in Japanese Patent Application Laid-Open Nos. 2001-275942 and 2005-211433, but this method is limited to measurement within a lumen and cannot fix the probe itself to the region to be measured in a stable state. According to the method of pressing the hood or the like against the region to be measured as in Japanese Patent Application Laid-Open Nos. 2008-054843 and 2001-275933, the leading end part of the probe is simply pressed against the region to be measured in a conventional case, and the probe is not set along the region to be measured in the axial direction. Further, there are problems that a load on an operator is large, the stability of probe fixation is low, and a skill of the operator is relied on. In addition, a method of using a needle, a clip, and the like to thereby fix the probe to the region to be measured can also be conceived, but it is not preferable to damage a human body.

Further, it is possible to conceive the method in which the pressure inside of the hood is reduced, and the hood is adsorbed onto the region to be measured, to thereby fix the probe to the region to be measured, but according to Japanese Patent Application Laid-Open Nos. 2004-000376 and 2003-144378, a target region is sucked into the hood, and hence damage to a human body is not zero. As an adsorptive power is stronger, a suction amount of the target region into the hood becomes larger to increase an influence on the human body. If the adsorptive power is made smaller by increasing an adsorption area or reducing the pressure itself inside of the hood, the influence on the human body can be reduced, but it becomes accordingly difficult to fix the probe to the region to be measured. Although Japanese Patent Application Laid-Open No. 2003-144378 proposes a method of providing a pressure sensor to thereby prevent the influence of adsorption on the human body, this does not radically improve the method of fixing the probe by adsorption.

The presently disclosed subject matter has been made in view of the above-mentioned circumstances, and therefore has an object to provide an endoscope hood which can fix, in the case of using a probe which is placed at a leading end of an insertion part of an endoscope so as to protrude therefrom and acquires data of a region to be measured in a direction substantially orthogonal to an axial direction, the probe to the region to be measured in a state where the probe is set therealong in the axial direction, and also can fix the probe to the region to be measured by adsorption without any influence on a human body.

In order to achieve the above-mentioned object, a first aspect of the presently disclosed subject matter provides an endoscope hood which is placed at a leading end of an insertion part of an endoscope, the insertion part on which a pass-through port through which an elongated probe can pass and a gas suction port configured to serve to suck gas from a leading end surface of the insertion part are provided, and the probe passing through the pass-through port to be placed so as to protrude from the leading end surface and acquiring data of a region to be measured in a direction substantially orthogonal to an axial direction of the probe, the endoscope hood including: an opening portion which is placed on a far side with respect to the leading end surface of the insertion part, wherein an opening is formed on the opening portion in a direction substantially orthogonal to an axial direction of the insertion part; and a flexible hood part configured to cover a portion other than the opening, on the far side with respect to the leading end surface of the insertion part, wherein gas inside of the hood part is sucked from the gas suction port, the opening is adsorbed onto the region to be measured, and the hood part is deformed so as to be closely adhered to the region to be measured within a range of the opening and the probe, to thereby fix the probe to the region to be measured in a state where the probe is set along the region to be measured.

According to the first aspect of the presently disclosed subject matter, in the case of using the probe which acquires the data of the region to be measured in the direction substantially orthogonal to the axial direction, the gas inside of the hood part is sucked, whereby the opening which is formed in the direction substantially orthogonal to the axial direction of the insertion part is adsorbed onto the region to be measured, and the hood part is deflated. As a result, the leading end of the insertion part is fixed to the region to be measured, and the probe is also fixed to the region to be measured while being set therealong in the axial direction. This makes it possible to enable the probe to acquire the data of the region to be measured in the direction substantially orthogonal to the axial direction, and also possible to enable the probe to follow the movement of the region to be measured caused by a body motion or the like, to thereby reduce blurring of the data. In addition, linear scanning in the axial direction of the probe can be performed with the leading end of the insertion part being kept fixed to the region to be measured, and hence it is possible to perform the linear scanning with high accuracy. Further, the hood part is deformed so as to be closely adhered to the region to be measured within the range of the opening, and hence it is possible to fix the probe to the region to be measured by the adsorption without any influence on a human body.

A second aspect of the presently disclosed subject matter provides an endoscope hood according to the first aspect, wherein a flexible member harder than the hood part is provided in a peripheral part of the opening. According to the second aspect of the presently disclosed subject matter, a portion of the hood part other than the peripheral part of the opening can be formed of a more flexible material. Accordingly, when the gas inside of the hood part is sucked, the hood part can be easily deformed so as to be closely adhered to the region to be measured, without sucking the region to be measured into the hood part.

A third aspect of the presently disclosed subject matter provides an endoscope hood according to the first or second aspect, wherein the hood part is optically transparent. According to the third aspect of the presently disclosed subject matter, in the case where an observation window is provided at the leading end of the insertion part, observation from the observation window is possible through the transparent hood part.

A fourth aspect of the presently disclosed subject matter provides an endoscope hood according to the third aspect, wherein: a gas supply port configured to supply gas from the leading end surface is provided on the insertion part, the insertion part includes an observation window which enables observation of a field of view on the far side with respect to the leading end surface, and the hood part is inflated by supplying gas into the hood part, at a time of the observation from the observation window. According to the fourth aspect of the presently disclosed subject matter, in the case of performing the observation from the observation window at the leading end of the insertion part, supplying of gas into the hood part makes it possible to prevent creases and the like of the hood part from obstructing the field of view.

A fifth aspect of the presently disclosed subject matter provides an endoscope hood according to any one of the first to fourth aspects, wherein: a gas supply port configured to supply gas from the leading end surface is provided on the insertion part, and the adsorption of the opening onto the region to be measured is cancelled by supplying gas into the hood part from the gas supply port. According to the fifth aspect of the presently disclosed subject matter, the adsorption of the hood part onto the region to be measured can be easily cancelled without any load on a human body.

A sixth aspect of the presently disclosed subject matter provides an endoscope hood according to any one of the first to fifth aspects, wherein a tubular part which is extendedly provided on a proximal end side of the hood part is fitted and fixed to an outer circumferential surface of the leading end of the insertion part, to thereby fix the hood part to the leading end of the insertion part. The sixth aspect of the presently disclosed subject matter describes one mode of setting the hood to the insertion part.

A seventh aspect of the presently disclosed subject matter provides an endoscope hood according to any one of the first to fifth aspects, wherein the hood part is formed in a leading end part of an over tube. The seventh aspect of the presently disclosed subject matter describes one mode of setting the hood to the insertion part.

An eighth aspect of the presently disclosed subject matter provides an endoscope hood according to any one of the first to seventh aspects, wherein the probe passes through a forceps channel of the insertion part to be placed so as to protrude from a forceps exit port on the leading end surface of the insertion part. The eighth aspect of the presently disclosed subject matter describes one example of a configuration for placing the probe at the leading end of the insertion part.

A ninth aspect of the presently disclosed subject matter provides an endoscope hood according to the eighth aspect, wherein: a center of the forceps exit port is located at a position different from that of a center of the leading end surface of the insertion part; and the opening of the hood is located in a direction in which the forceps exit port is provided, with respect to the center of the leading end surface of the insertion part. The forceps exit port is located in relation to a position at which the probe is placed at the leading end of the insertion part, and the opening of the hood is located correspondingly to the forceps exit port.

A tenth aspect of the presently disclosed subject matter provides an endoscope hood according to any one of the first to ninth aspects, wherein the probe is a flexible probe. According to the tenth aspect of the presently disclosed subject matter, when the gas inside of the hood part is sucked, the probe is pressed by the hood part toward the region to be measured. At this time, in the case of using the flexible probe, the probe is bent to be directly pressed against the region to be measured. As a result, the probe can be more reliably fixed to the region to be measured.

An eleventh aspect of the presently disclosed subject matter provides an endoscope hood according to any one of the first to tenth aspects, wherein switching can be made between a state where the opening is fitted to the leading end surface of the insertion part and a state where the opening is faced in the direction substantially orthogonal to the axial direction of the insertion part. According to the eleventh aspect of the presently disclosed subject matter, when the probe is not used, the opening is fitted to the leading end of the insertion part, whereby the field of view from the observation window can be secured.

A twelfth aspect of the presently disclosed subject matter provides an endoscope hood according to any one of the first to eleventh aspects, wherein the probe is used for data acquisition in one of an optical tomographic imaging apparatus and an ultrasonic diagnostic apparatus. The twelfth aspect of the presently disclosed subject matter describes one mode of a type of the probe for which the endoscope hood according to the presently disclosed subject matter is used, and is mainly intended to fix, to the region to be measured, the probe used for diagnostic imaging in the optical tomographic imaging apparatus or the ultrasonic diagnostic apparatus.

According to the presently disclosed subject matter, in the case of using the probe which is placed at the leading end of the insertion part of the endoscope so as to protrude therefrom and acquires the data of the region to be measured in the direction substantially orthogonal to the axial direction, it is possible to fix the probe to the region to be measured in the state where the probe is set therealong in the axial direction (or, in the state where the probe is abutted thereagainst in the axial direction), and also possible to fix the probe to the region to be measured by adsorption without any influence on a human body.

DETAILED DESCRIPTION OF THE PREFERRED EMBODIMENT

Hereinafter, an endoscope hood according to a preferred embodiment of the presently disclosed subject matter is described in detail with reference to the accompanying drawings.

Figure 1:
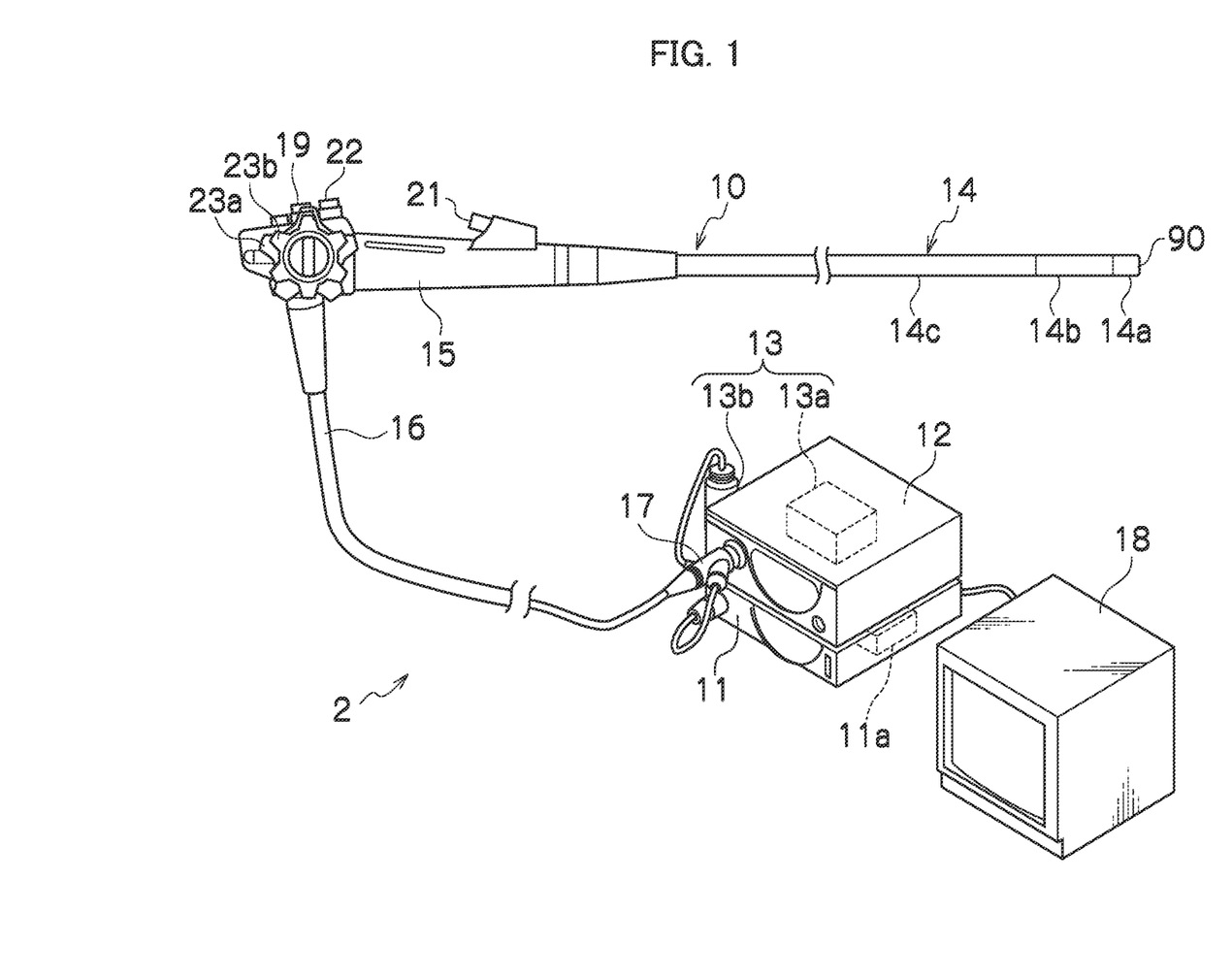
FIG. 1 is an overall configuration view illustrating an endoscope system.

FIG. 1 is an overall configuration view illustrating an endoscope system. An endoscope system 2 illustrated in FIG. 1 includes an endoscope apparatus (endoscope) 10, a processor apparatus 11, a light source apparatus 12 and an air supply/water supply apparatus 13. The air supply/water supply apparatus 13 includes an air supply pump 13a incorporated in the light source apparatus 12 and a washing water tank 13b provided outside of the light source apparatus 12.

The endoscope 10 includes an insertion part 14, an operation part 15, and a universal code 16. The insertion part 14 is a part to be inserted into a body cavity of a patient (body to be examined), and includes a leading end part 14a, a bending part 14b, and a flexible tube part 14c which are connected in the stated order from the leading end side (the opposite side to the operation part 15).

Figure 2:
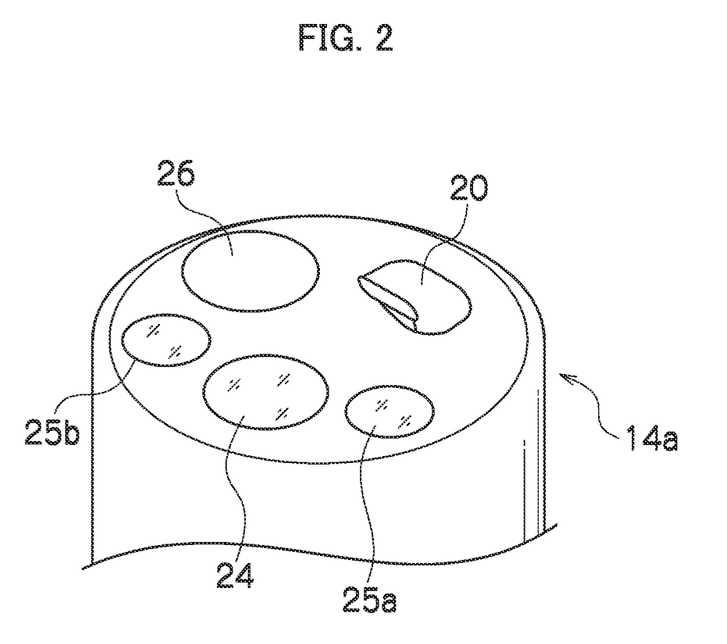
FIG. 2 is an enlarged perspective view illustrating a leading end of an insertion part.

The leading end part 14a is a part including a leading end surface 90 which is a leading end of the insertion part 14, and an image pickup part including image pickup elements such as a CCD (charge-coupled device) and a CMOS (complementary metal-oxide semiconductor) and a lens is provided inside of the leading end part 14a. As illustrated in FIG. 2, an observation window 24, illumination windows 25a and 25b, a forceps exit port 26, and an injection nozzle 20 are provided on the leading end surface 90.

The observation window 24 is formed of an opening formed on the leading end surface 90 and a transparent window member set to the opening, and subject light taken in from the observation window 24 is guided to the image pickup part provided inside of the leading end part 14a, whereby photographing on a front side of the leading end part 14a is performed.

The illumination windows 25a and 25b are formed of openings on both sides of the observation window 24 and transparent window members set to the respective openings. The illumination light is guided to a light emitting part of the leading end part 14a by a light guide, which passes from the light source apparatus 12 through the insides of the universal code 16, the operation part 15, and the insertion part 14 of the endoscope 10, and then is radiated forward (on the far side) from the illumination windows 25a and 25b, so that the subject in front thereof is illuminated.

The forceps exit port 26 corresponds to an opening portion on the leading end surface 90 side, which is communicated with a forceps port 21 of the operation part 15 via a forceps channel passing through the inside of the insertion part 14, and various treatment tools and a probe inserted from the forceps port 21 are exposed at the forceps exit port 26 in front (on the far side) of the leading end surface 90. In addition, the forceps exit port 26 is also connected to a suction apparatus (not illustrated) via a suction channel coupled to the forceps channel, and air or washing water injected from the injection nozzle 20, waste matters inside of the body to be examined, and the like are sucked from the forceps exit port 26 into the suction apparatus.

The injection nozzle 20 is attached to an opening formed on the leading end surface 90. The air or the washing water is guided by an air supply/water supply channel which passes from the air supply pump 13a or the washing water tank 13b through the insides of the universal code 16, the operation part 15, and the insertion part 14, and then is injected by the injection nozzle 20 in the direction of the observation window 24, whereby washing of the observation window 24 and the like are performed.

The operation part 15 is a part provided with operation members for allowing an operator to perform various operations, and includes the forceps port 21, an air supply/water supply button 22, a suction button 19, a vertical angle knob 23a, a horizontal angle knob 23b, and the like.

As described above, the forceps port 21 is communicated with the forceps exit port 26 via the forceps channel, and the various treatment tools and the probe to be protruded from the forceps exit port 26 are inserted therein.

The air supply/water supply button 22 is an operation button for performing injection start and injection stop of the air or the washing water from the injection nozzle 20 by operating a valve of the air supply/water supply channel. The suction button 19 is an operation button for performing suction start and suction stop from the forceps exit port 26 by operating a valve of the suction channel.

The vertical angle knob 23a and the horizontal angle knob 23b are coupled to a wire insertedly provided in the insertion part 14, and when the knobs 23a and 23b are operated, the wire is pushed or pulled, and the bending part 14b is accordingly bent in a vertical or horizontal direction.

The universal code 16 has one end to which a connector 17 is attached. The connector 17 is a combination connector, and is connected to each of the processor apparatus 11 and the light source apparatus 12. A cable which connects the image pickup part at the leading end of the insertion part 14 with the processor apparatus 11, the light guide which connects the light emitting part at the leading end of the insertion part 14 with the light source apparatus 12, the air supply/water supply channel which connects the injection nozzle 20 at the leading end of the insertion part 14 with the air supply/water supply apparatus 13 (the air supply pump 13a and the washing water tank 13b), and the like are insertedly provided inside of the universal code 16.

The processor apparatus 11 acquires an image pickup signal from the image pickup part (image pickup elements) of the endoscope 10 (leading end part 14a). Then, the processor apparatus 11 performs various types of image processing on the acquired image pickup signal, to thereby create an endoscope image. In addition, the processor apparatus 11 transmits a drive control signal for controlling the drive of the image pickup elements to the image pickup part.

The endoscope image created by the processor apparatus 11 is displayed on a monitor 18 connected to the processor apparatus 11 via a cable.

In addition, a controller 11a which is formed of a CPU (central processing unit) and a memory and controls the respective parts of the apparatus is provided inside of the processor apparatus 11. The processor apparatus 11 is connected to the light source apparatus 12 via a communication cable, and the controller 11a communicates various pieces of control information with the light source apparatus 12.

The light source apparatus 12 includes a white color light source, and the light emitted from the light source enters the light guide inside of the endoscope 10 connected thereto via the connector 17. With this configuration, the illumination light is transmitted by the light guide to the light emitting part of the endoscope 10 (leading end part 14a), and then is emitted from the light emitting part via the illumination windows 25a and 25b.

The air supply/water supply apparatus 13 includes the air supply pump 13a incorporated in the light source apparatus 12 and the washing water tank 13b provided outside of the light source apparatus 12. The air supply pump 13a and the washing water tank 13b are connected to the air supply/water supply channel inside of the endoscope 10 via the connector 17. When the air supply/water supply button 22 of the operation part 15 is operated, the injection from the injection nozzle 20 at the leading end of the insertion part 14 can be switched between the air from the air supply pump 13a and the washing water from the washing water tank 13b.

Figure 3:
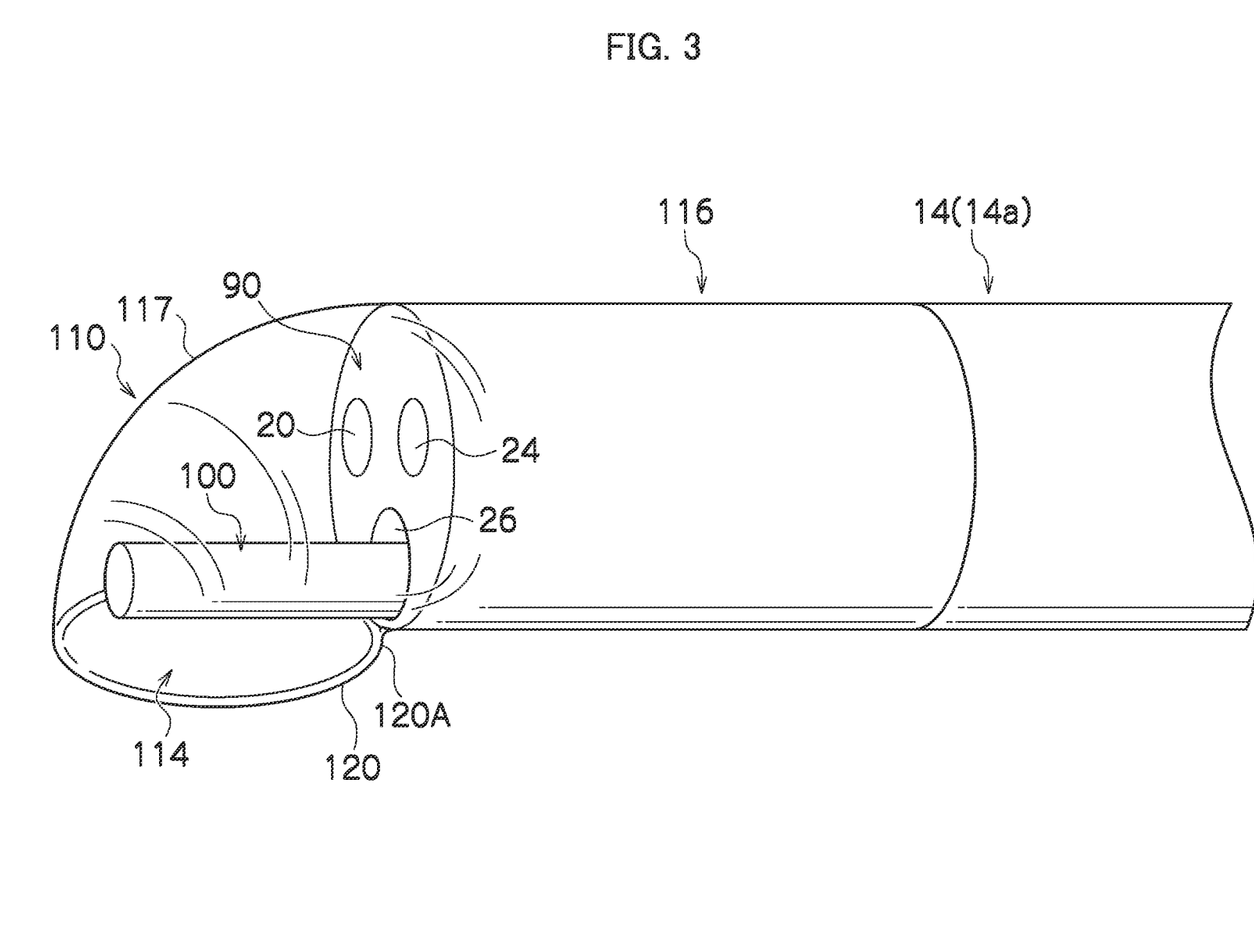
FIG. 3 is a perspective view illustrating a configuration of a hood attached to the leading end of the insertion part.

FIG. 3 is a perspective view illustrating a configuration of the hood according to the presently disclosed subject matter, which is attached to the leading end part 14a of the insertion part 14 in the endoscope 10 described above.

In the leading end part 14a of the insertion part 14 (the leading end of the insertion part 14) of FIG. 3, the injection nozzle 20, the observation window 24, and the forceps exit port 26 on the leading end surface 90 of FIG. 2 are briefly illustrated, and the probe 100 is placed so as to protrude forward with respect to the leading end surface 90. In the present embodiment, the probe 100 is an optical probe for OCT used for acquiring data of a region to be observed (region to be measured) in an optical tomographic imaging apparatus which creates an optical tomographic image of the region to be measured. The probe 100 corresponds to a leading end portion of an elongated insertion part which is connected to the optical tomographic imaging apparatus and is inserted from the forceps port 21. At least the leading end portion of the insertion part, which is used as the probe, is covered by a transparent flexible external cylinder (sheath), and an optical fiber passes through the inside of the insertion part. A proximal end of the optical fiber is connected to a connector of a main body (processor) of the optical tomographic imaging apparatus (not illustrated), and the leading end thereof includes, at a portion of the probe 100, an optical system which emits a signal beam from the optical fiber to the region to be measured and takes a return beam from the region to be measured into the optical fiber. This optical system includes, for example, an optical mirror which reflects the signal beam emitted from the optical fiber in the axial direction of the probe 100, and the signal beam is emitted by the optical mirror in the direction substantially orthogonal to the axial direction of the probe 100, so that data of the region to be measured in this direction is acquired. In addition, the optical mirror can rotate inside of the sheath, to thereby rotate an emitting direction of the signal beam in a circumferential direction, which makes it possible to perform radial scanning. Further, the optical system can move in the axial direction of the probe 100 inside of the sheath, to thereby move an emitting position (illuminating position) of the signal beam in the axial direction, which makes it possible to perform linear scanning. At the time of data acquisition, the probe 100 is inserted from the forceps port 21 provided in the operation part 15 of the endoscope 10, passes through the forceps channel, and is guided to a position at which the probe 100 protrudes outwardly forward from the forceps exit port 26. It should be noted that the presently disclosed subject matter can be adopted as long as the probe 100 is configured to acquire data of the region to be measured in the direction substantially orthogonal to the axial direction, and hence the probe 100 does not necessarily need to be capable of radial scanning, and does not necessarily need to be capable of linear scanning.

Figure 4:
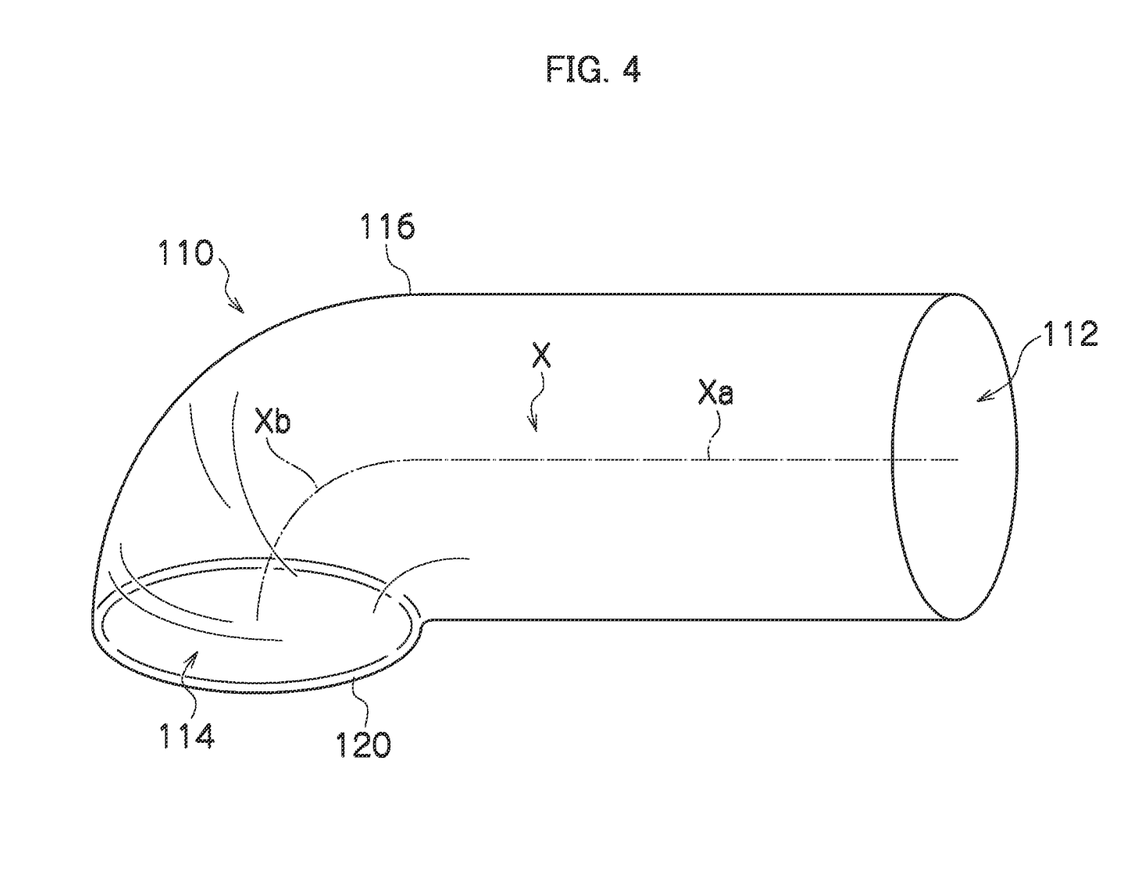
FIG. 4 is a perspective view illustrating a configuration of only the hood.

On the other hand, in the case where the probe 100 is used to perform measurement, a hood 110 is attached to the leading end of the insertion part 14 as illustrated in FIG. 3, and serves to fix the probe 100 to the region to be measured in the state where the probe 100 is set therealong in the axial direction. A substantial entirety of the hood 110 is formed of a flexible member which is transparent and flexible (a member which is softer than at least the region to be measured), and the hood 110 is formed into a shape as illustrated in FIG. 4. It should be noted that it is desirable to adopt, as a material of the hood 110, a material having high flexibility such as silicone and urethane which are also used as a material of a balloon attached to the insertion part, and having high transparency unlike other material of the balloon such as natural rubber.

As illustrated in FIG. 4, the hood 110 has a shape obtained by sweeping, along a central axis X thereof, a circular ring on a plane orthogonal to the central axis X. The central axis X is defined by connecting a straight line part Xa and a circular arc part Xb having a central angle of approximately 90 degrees. In addition, end parts on the proximal end side and the leading end side of the hood 110 corresponding to the proximal end side and the leading end side of the central axis X are opened as openings 112 and 114, respectively. A ring-like part 120 which is formed into a ring-like shape of a material (a material having elasticity such as rubber) harder than the flexible member forming the substantial entirety of the hood 110 is provided in a peripheral part of the opening 114 on the leading end side. It should be noted that a portion other than the ring-like part 120, which is formed of the flexible member, is referred to as a flexible part 116, and a portion of the flexible part 116 which protrudes forward with respect to the leading end surface 90 when the hood 110 is attached to the leading end of the insertion part 14 as illustrated in FIG. 3 is referred to as a hood part 117. In addition, the shape of the hood part 117 is not limited to that of the present embodiment, and any shape may be adopted as long as a portion other than the opening 114 on the forward side of the leading end surface 90 of the insertion part 14 is covered. In addition, it is preferable to use a resin material (PC (Polycarbonate), POM (polyoxymethylene)) as a material of the ring-like part 120.

As illustrated in FIG. 3, an outer circumferential part of the leading end of the insertion part 14 is covered by the opening 112 on the proximal end side of the hood 110, and the hood 110 is attached to the leading end of the insertion part 14 with the use of a medical tape or the like. In addition, as illustrated in FIG. 3, the hood 110 is attached to the leading end of the insertion part 14 so that the opening 114 (ring-like part 120) on the leading end side of the hood 110 is positioned on the forward side of the leading end surface 90 of the insertion part 14 and that an end point 120A on the most proximal side of the ring-like part 120 is located at a position substantially coincident with the periphery of the leading end surface 90. Further, the hood 110 is attached thereto so that the opening 114 is positioned on the probe 100 side with respect to a central axis of the insertion part 14, that is, in a direction in which the forceps exit port 26 is provided, when viewed from the front side (leading end side) of the leading end surface 90 of the insertion part 14. It should be noted that the hood 110 may be formed at a leading end of a so-called over tube which guides the insertion part 14 of the endoscope 10 to the inside of the cavity of the body to be examined and entirely covers the insertion part 14.

Figure 5:
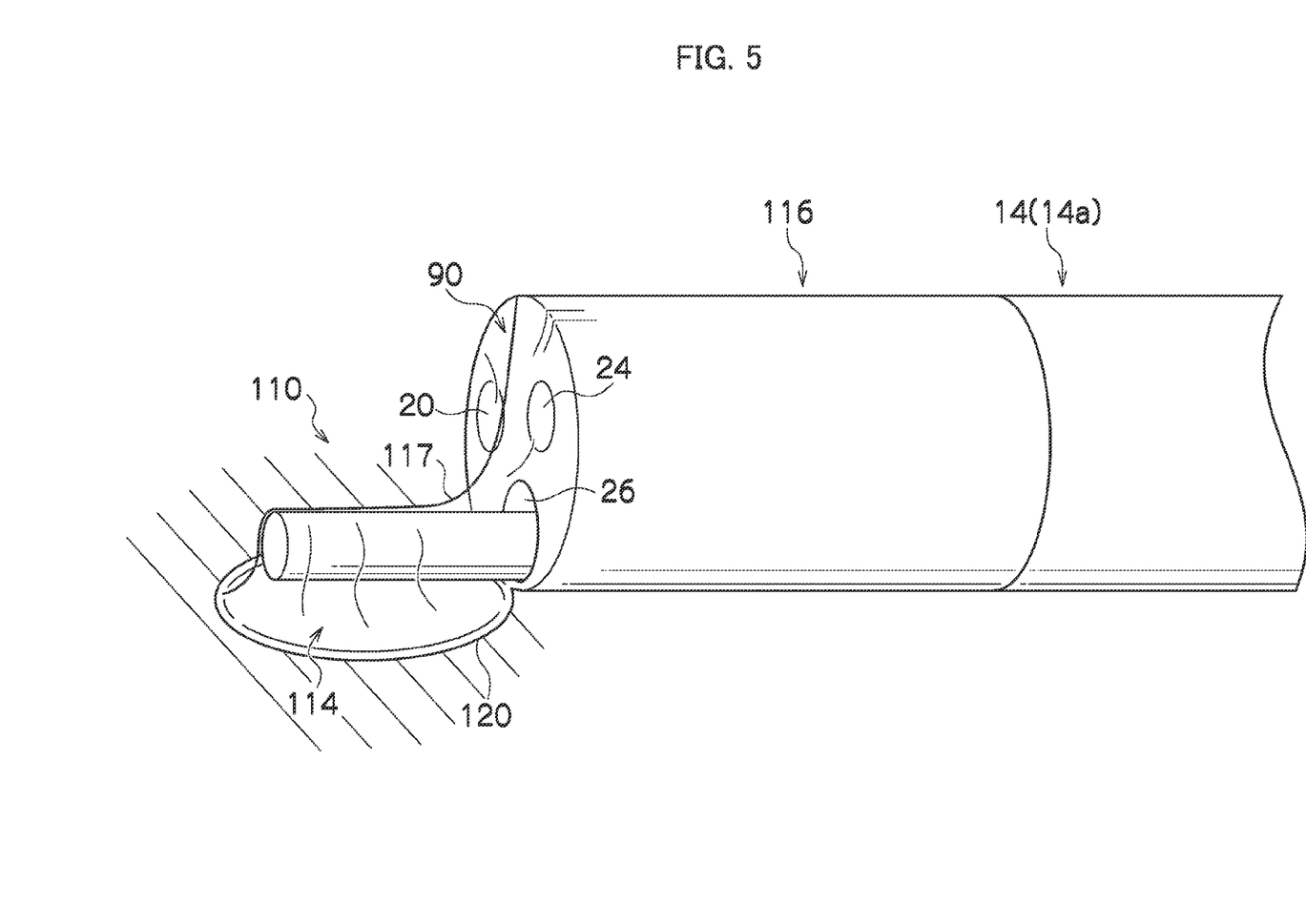
FIG. 5 is a perspective view illustrating a state where the hood is deflated compared with FIG. 3.

In the state where the opening 114 (ring-like part 120) of the hood part 117 is brought closer to the region to be measured, suction (air suction) from the forceps exit port 26 is carried out by using a suction apparatus. As a result, as illustrated in FIG. 5, the pressure inside of the hood 110 (inside of the hood part 117) is reduced, and the opening 114 (ring-like part 120) adsorbs onto a surface of the region to be measured, so that the pressure inside of the hood 110 is further reduced. Then, the hood part 117 shrinks so as to gather onto a plane defined by the ring-like part 120 (opening 114) harder than the hood part 117. That is, the hood part 117 deforms so as to be closely adhered to the region to be measured within a range of the opening 114 and the probe 100, and presses the probe 100 to the opening 114 side so as to remove a gap between the probe 100 and the region to be measured. As a result, the leading end of the insertion part 14 is fixed to the region to be measured, and the probe 100 is held and fixed by the hood part 117 while being set along the axial direction. At this time, the hood part 117 is sufficiently softer than the region to be measured, and thus has a curved surface shape which can shrink substantially flatly along a surface of the opening 114. Therefore, the region to be measured is hardly sucked into the hood part 117 to protrude, and hence there is almost no influence on a human body. In addition, the hood part 117 is adsorbed so as to include a range of the probe 100 set along the axial direction, and hence an adsorption area can be made larger. Accordingly, it is possible to obtain a large adsorptive power as a whole while making a local suction power small, and hence the probe 100 can be reliably fixed to the region to be measured.

It should be noted that, in the present embodiment, the probe 100 is flexible and bendable (elastically deformable), and hence when the hood part 117 deflates, the probe 100 is fixed while being pressed against the surface of the region to be measured. In addition, when air is supplied from the injection nozzle 20 into the hood part 117 in the state of FIG. 5, the hood part 117 inflates as illustrated in FIG. 3, so that the adsorption between the ring-like part 120 and the region to be measured is cancelled.

Description is given of an operation when the hood 110 is attached to the insertion part 14 as described above and the probe 100 is used to acquire data of the region to be measured inside of the cavity of the body to be examined.

First, as illustrated in FIG. 3, the hood 110 is attached to the leading end of the insertion part 14. Then, with the probe 100 being placed so as not to protrude from the leading end of the insertion part 14, the insertion part 14 is inserted into the cavity of the body to be examined. At this time, if the hood part 117 of the hood 110 shrinks, photographing through the observation window 24 is hindered by creases. Therefore, air is supplied from the injection nozzle 20 as appropriate, to thereby inflate the hood part 117. When the leading end of the insertion part 14 reaches the region to be measured, the probe 100 is inserted into the forceps port 21 so that the leading end of the insertion part 14 is exposed at the forceps exit port 26, as illustrated in FIG. 3.

Subsequently, with the ring-like part 120 of the hood 110 being pressed against (brought closer to) the region to be measured, the air inside of the hood part 117 is sucked from the forceps exit port 26 by using the suction apparatus, and the ring-like part 120 is adsorbed onto the surface of the region to be measured. As a result, the leading end of the insertion part 14 is fixed to the region to be measured. Then, the air inside of the hood part 117 is continuously sucked even after the adsorption, the hood part 117 is shrunk (deflated) to be closely adhered to the region to be measured within the range of the opening 114 and the probe 100, and the probe 100 is thus pressed against the region to be measured via the opening 114. As a result, the probe 100 is held and fixed by the hood part 117 setting therealong in the axial direction (or, while abutting against the region to be measured in the axial direction), and the data acquisition of the region to be measured in the direction substantially orthogonal to the probe 100 becomes possible.

After that, the data acquisition of the region to be measured using the probe 100 is started. At this time, because the probe 100 is held and fixed by the hood part 117 while being set along the region to be measured in the axial direction, even when a position of the region to be measured changes due to a body motion, the probe 100 follows this change. Accordingly, a distance between the probe 100 and the surface of the region to be measured is kept constant, so that the data acquisition is performed with accuracy.

In addition, in the case as in the present embodiment where the probe 100 is an optical probe for OCT, even when the optical system which is provided inside of the sheath and emits a signal beam is moved in the axial direction, to thereby perform scanning (linear scanning) on a scan region within a predetermined range in the axial direction, a leading end of the leading end part 14a and the probe 100 can be kept fixed to the region to be measured during the scanning. Therefore, a created optical tomographic image is not blurred (disturbed), and it is possible to perform the linear scanning with a high positional accuracy of the data acquisition position. Instead of moving the optical system inside of the sheath in the axial direction to thereby move the measurement position in the axial direction, in the case of moving the entire probe 100 (together with the sheath) to thereby perform the linear scanning, the probe 100 is moved with the reduced pressure (suction) state inside of the hood part 117 being kept, or after the probe 100 has been moved by supplying a slight amount of air from the injection nozzle 20 into the hood part 117, the air inside of the hood 110 is sucked again. In this way, the measurement position can be moved in the axial direction with the leading end of the insertion part 14 being fixed to the region to be measured. Therefore, it is similarly possible to perform the linear scanning with a high positional accuracy of the data acquisition position.

Figure 6:
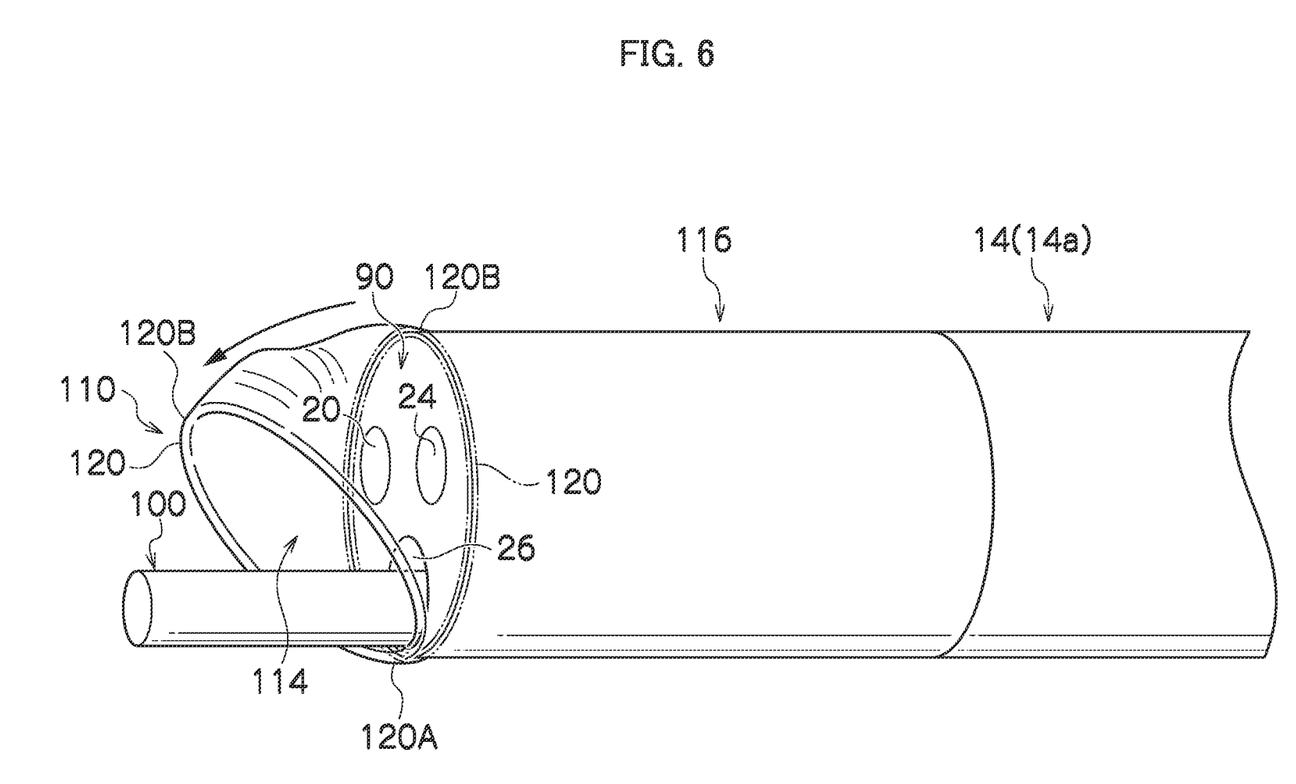
FIG. 6 is a perspective view illustrating a configuration of an application example of the hood attached to the leading end of the insertion part illustrated in FIG. 3.

In the above-mentioned embodiment, the ring-like part 120 of the hood 110 may be detachably attached to the peripheral part of the leading end of the insertion part 14 (the peripheral part of the leading end surface 90). That is, switching may be possible between the state where the opening 114 of the hood 110 is fitted to the leading end surface 90 of the insertion part 14 and the state illustrated in FIG. 3. For example, with reference to FIG. 6, the ring-like part 120 of the hood 110 (the peripheral part of the opening 114) is attached to the leading end of the insertion part 14 so as to be swingable with respect to the end point 120A on the proximal end side as a fulcrum point. Then, an attachment/detachment device which enables the ring-like part 120 of the hood 110 to be detachably attached to the peripheral part of the leading end of the insertion part 14 is provided at a portion other than the end point 120A of the ring-like part 120 (for example, an end point 120B on the leading end side of the ring-like part 120). When the attachment/detachment device is brought into an attached state, the ring-like part 120 of the hood 110 is attached to the peripheral part of the leading end of the insertion part 14. It should be noted that a bonding device which can be easily peeled off may be adopted instead of the attachment/detachment device. In addition, a cancellation device which cancels the attached state of the attachment/detachment device or a bonded state of the bonding device may be arbitrarily selected. For example, in the state where the ring-like part 120 of the hood 110 is attached to the peripheral part of the leading end of the insertion part 14 (in the state where the opening 114 is fitted to the leading end surface 90 of the insertion part 14), a cancellation member (a protruding piece or the like) coupled to the ring-like part 120 is placed at the forceps exit port 26. With this configuration, when the probe 100 is protruded from the forceps exit port 26, the cancellation member is pushed by the probe 100, so that the attached state of the attachment/detachment device or the bonded state of the bonding device can be cancelled. In the hood 110 thus configured, the ring-like part 120 of the hood 110 is kept attached to the peripheral part of the leading end of the insertion part 14 until the insertion part 14 inserted into the body cavity reaches the region to be measured, that is, until the data acquisition is started. In this way, the hood 110 (hood part 117) does not exist in front of the observation window 24, whereby an observation image having an excellent field of view can be obtained. Then, at the start of the data acquisition, the ring-like part 120 of the hood 110 is detached from the leading end of the insertion part 14, and the hood 110 (hood part 117) is shifted to the state illustrated in FIG. 3 to be used as described in the above-mentioned embodiment.

In addition, in the above-mentioned embodiment, the optical probe for OCT is exemplified as the probe 100, but the presently disclosed subject matter is effective even in a probe of other diagnostic imaging apparatus such as an ultrasonic probe used in an ultrasonic diagnostic apparatus, and is also effective in a probe of a measurement apparatus other than the diagnostic imaging apparatus.

In addition, in the above-mentioned embodiment, the hood part 117 of the hood 110 is formed of an optically transparent member, but does not necessarily need to be transparent.

In addition, in the above-mentioned embodiment, the substantial entirety of the hood part 117 and the like of the hood 110 is formed of the flexible member which is flexible, such as a nylon film, and the ring-like part 120 harder than the flexible member is provided in the peripheral part of the opening 114. Alternatively, the entirety of the hood 110 is formed of a material having a hardness which is high enough to maintain the shape of the opening 114 and a hardness which allows the hood part 117 to shrink in the same manner as in the above-mentioned embodiment when the air inside of the hood part 117 is sucked, whereby it is possible to eliminate the need to provide the ring-like part 120 formed of a material different from that of the hood part 117.

In addition, in the above-mentioned embodiment, because the probe 100 is a flexible probe, when the air inside of the hood part 117 is sucked, the probe 100 is fixed to the region to be measured while abutting against (being pressed against) the surface of the region to be measured in the axial direction. In the case where the probe 100 is not close to the region to be measured (the forceps exit port 26 is provided near the center of the leading end of the insertion part 14) or in the case where the probe 100 is configured by a sheath of a hard material, even when the air inside of the hood part 117 is sucked to thereby deflate the hood part 117, the probe 100 may not abut against the region to be measured. However, even in this case, the air inside of the hood part 117 is sucked, and accordingly the hood part 117 deflates (deforms) so as to be closely adhered to the region to be measured within the range of the opening 114 and the probe 100, so that the probe 100 is held and fixed by the hood part 117 to the region to be measured. Accordingly, the hood 110 according to the above-mentioned embodiment is effective irrespective of the configuration of the probe 100. In addition, instead of the probe 100 which passes through the forceps channel to be placed so as to protrude from the forceps exit port 26, it is possible to adopt the probe 100 which is attached to the leading end of the insertion part 14 by a predetermined attachment device.

In addition, in the above-mentioned embodiment, the air inside of the hood 110 is supplied and sucked by using a supply device of air from the injection nozzle 20 and a suction device of air from the forceps exit port 26, which are devices essentially provided for a general endoscope, but these devices are given as a mere example. Therefore, other device may be used, or a special device which supplies and sucks the air inside of the hood 110 may be provided.

What is claimed is:
1. An endoscope apparatus comprising:
   an endoscope having an insertion part, the insertion part having a distal end part having a distal end surface, the insertion part having a pass-through port through which an elongated probe can pass and further having a gas suction port configured to suck gas from the distal end surface of the insertion part, the probe passing through the pass-through port so as to protrude from the distal end surface and acquire data of a region to be measured in a direction substantially orthogonal to an axial direction of the probe, and a flexible endoscope hood connected to the distal end part of said endoscope and including:

an extended section that extends from the distal end part of the insertion part of the endoscope, said extended section having an opening portion that includes an opening formed in a direction substantially orthogonal to an axial direction of the insertion part, and;

a flexible hood part positioned between the opening portion and the distal end surface of the insertion part; and a hood attachment part overlapping an outer surface region of the distal end part of the insertion part and attaching the flexible endoscope hood to the insertion part, wherein gas inside of the flexible hood part is sucked from the gas suction port, the flexible hood part is collapsible to conform to an exterior surface of the probe protruding from the distal end surface of the insertion part such that the probe is fixed relative to the region to be measured and the opening is adsorbed to the region to be measured.

2. The endoscope apparatus according to claim 1, wherein a flexible member harder than the flexible hood part is provided in a peripheral part of the opening.

3. The endoscope apparatus according to claim 1, wherein the flexible hood part is optically transparent.

4. The endoscope apparatus according to claim 3, wherein:
a gas supply port configured to supply gas from the distal end surface is provided on the insertion part,
the insertion part includes an observation window which enables observation of a field of view on the far side with respect to the distal end surface, and
the flexible hood part is inflated by supplying gas into the flexible hood part, at a time of the observation from the observation window.

5. The endoscope apparatus according to claim 1, wherein:
a gas supply port configured to supply gas from the distal end surface is provided on the insertion part, and
the adsorption of the opening onto the region to be measured is cancelled by supplying gas into the flexible hood part from the gas supply port.

6. The endoscope apparatus according to claim 1, wherein said hood attachment part is a tubular part extendedly provided on a proximal end side of the flexible hood part, said hood attachment part being fitted and fixed to an outer circumferential surface of the distal end part of the insertion part, to thereby fix the endoscope hood to the insertion part.

7. The endoscope apparatus according to claim 1, wherein the flexible hood part is formed in a leading end part of an over tube.

8. The endoscope apparatus according to claim 1, wherein the probe passes through a forceps channel of the insertion part to be placed so as to protrude from a forceps exit port on the distal end surface of the insertion part.

9. The endoscope apparatus according to claim 8, wherein:
a center of the forceps exit port is located at a position different from that of a center of the distal end surface of the insertion part; and
the opening of the endoscope hood is located in a direction in which the forceps exit port is provided, with respect to the center of the distal end surface of the insertion part.

10. The endoscope apparatus according to claim 1, wherein the probe is a flexible probe.

11. The endoscope apparatus according to claim 1, wherein switching can be made between a state where the opening is fitted to the distal end surface of the insertion part and a state where the opening is faced in the direction substantially orthogonal to the axial direction of the insertion part.

12. The endoscope apparatus according to claim 1, wherein the probe is used for data acquisition in one of an optical tomographic imaging apparatus and an ultrasonic diagnostic apparatus.

* * * * *